US007309811B2

(12) United States Patent
McConlogue et al.

(10) Patent No.: US 7,309,811 B2
(45) Date of Patent: Dec. 18, 2007

(54) TRANSGENIC MICE KNOCKOUTS OF BACE-1

(75) Inventors: Lisa McConlogue, Burlingame, CA (US); Mark E. Gurney, Reykjavik (IS)

(73) Assignees: Elan Pharmaceuticals, Inc, South San Francisco, CA (US); Pharmacia & Upjohn Company, Kalamazoo, MI (US)

( * ) Notice: Subject to any disclaimer, the term of this patent is extended or adjusted under 35 U.S.C. 154(b) by 63 days.

(21) Appl. No.: 10/082,804

(22) Filed: Feb. 22, 2002

(65) Prior Publication Data

US 2002/0194632 A1 Dec. 19, 2002

Related U.S. Application Data

(60) Provisional application No. 60/293,762, filed on May 25, 2001, provisional application No. 60/271,514, filed on Feb. 26, 2001, provisional application No. 60/271,092, filed on Feb. 23, 2001.

(51) Int. Cl.
  *A01K 67/027* (2006.01)
  *A01K 67/033* (2006.01)
  *G01N 33/00* (2006.01)
  *C12N 15/00* (2006.01)
  *C12N 5/00* (2006.01)
(52) U.S. Cl. .................. 800/18; 800/3; 800/8; 800/12; 800/25; 435/354
(58) Field of Classification Search .................. 800/3, 800/12, 13–18, 25, 24, 28, 8; 435/325, 354
See application file for complete search history.

(56) References Cited

U.S. PATENT DOCUMENTS

| 4,666,829 | A | 5/1987 | Glenner et al. |
| 5,612,486 | A | 3/1997 | McConlogue et al. |
| 5,811,231 | A | 9/1998 | Farr et al. |
| 6,040,138 | A | 3/2000 | Lockhart et al. |
| 6,114,133 | A | 9/2000 | Seubert et al. |
| 6,204,061 | B1 | 3/2001 | Capecchi et al. |
| 2002/0157122 | A1* | 10/2002 | Wong et al. .................. 800/12 |

FOREIGN PATENT DOCUMENTS

| WO | WO 97/07669 | 3/1997 |
| WO | WO97/07669 | 3/1997 |
| WO | WO 98/30683 | 7/1998 |
| WO | WO98/30683 | 7/1998 |
| WO | WO98/37183 | 8/1998 |
| WO | WO 98/37183 | 8/1998 |
| WO | WO98/39416 | 9/1998 |
| WO | WO 98/39416 | 9/1998 |
| WO | WO99/37143 | 7/1999 |
| WO | WO 99/37143 | 7/1999 |
| WO | WO 00/17369 | 3/2000 |
| WO | WO 00/47618 A | 8/2000 |
| WO | WO 00/72880 | 12/2000 |

OTHER PUBLICATIONS

Simerly, C. et al. Molecular Correlates of Primate Nuclear Transfer Failures. Science. Apr. 11, 2003, vol. 300, p. 297.*
Mitalipov et al. Rheusus Monkey Embryos Produced by Nuclear Transfer from Embryonic Blastomeres or Somatic Cells. Biology of Reproduction. 2002, vol. 66, pp. 1367-1373.*
Polejaeva et al. Cloned Pigs Produced by Nuclear Transfer from Adult Somatic Cells. Nature. Sep. 7, 2000, vol. 407, pp. 86-90.*
Pennisi et al. Clones: A Hard Act to Follow. Science. Jun. 9, 2000, vol. 288, pp. 1722-1727.*
Westhusin et al. Clonin gto Reproduce Desired Genotypes. Theriogenology. 2001, vol. 55, pp. 35-49.*
Meirelles et al. Complete Replacement of the Mitochondrial Genotype in a Bos indicus Calf Reconstructed by Nuclear Transfer to a Bos taurus Oocyte. Genetics 2001, vol. 158, pp. 351-356.*
Fehilly et al. Cytogenetic and Blood Group Studies of Sheep/Goat Chimaeras. J. Reprod. Fertility. 1985, vol. 74, pp. 215-221.*
Denning, C. et al. Gene Targeting in Primary Fetal Fibroblasts from Sheep and Pig. Cloning and Stem Cells. 2001, vol. 3, O. 4, pp. 221-231.*
Wheeler, M. B. et al. Transgenic Technology and Applications in Swine. Theriogenology. 2001, vol. 56, pp. 1345-1369.*
Moreadith, R. W. Gene Targeting in Embryonic Stem Cells: the New Physiology and Metabolism. J. Molecular Med. 1997, vol. 75, pp. 208-216.*
Prelle, K. et al. Establishment of Pluripotent Cell Lines from Vertebrate Species—Present Status and Future Prospects. Cells Tissues Organs. 1999, vol. 165, pp. 220-236.*
Gardner, R. L. et al. Reflections on the Biology of Embryonic Stem Cells. Internat. J. Devel. 1997, vol. 41, pp. 235-243.*
Games D. et al. Alzheimer-Type Neuropathology in Transgenic Mice Overexpressing V717F Beta-Amlyloid Precursor Protein. Nature. Feb. 9, 1995, vol. 373, pp. 523-527.*
Mansour, S. L. et al. Disruption of the Proto-Oncogene Int-2 in Mouse Embryo-Derived Stem Cells: A General Strategy for Targeting Mutations to Non-Selectable Genes. Nature. Nov. 24, 1988 vol. 336, pp. 348-352.*
Farhangrazi, Z. S. et al. High Density Lipoprotein Decreases Beta-Amyloid Toxicity in Cortical Cell Culture. NeuroReport. Mar. 24, 1997, vol. 8, No. 5, pp. 1127-1130.*
Cllark, A. J. et al. Gene Targeting in Livestock: A Preview. Transgenic Research. 2000, vol. 9, pp. 263-275.*

(Continued)

*Primary Examiner*—Deborah Crouch
(74) *Attorney, Agent, or Firm*—McDonnell Boehnen Hulbert & Berghoff LLP

(57) ABSTRACT

The invention provides transgenic animals that are heterozygous or homozygous for a nonfunctional allele of BACE-1. These animals show normal development indicating that BACE-1 is not necessary for development and hence is an appropriate therapeutic target. The transgenic animals are useful in various screening assays including identifying inhibitors of other enzymes involved in processing of APP to Aβ and determining a toxicity profile of inhibitors of BACE-1.

44 Claims, 8 Drawing Sheets

OTHER PUBLICATIONS

Farzan et al. BACE2, a Beta Seretase Homolog, Cleaves a the Beta Site and within the Amyloid-Beta Region of the Amyolid-Beta Precursor Protein. Proceedings National Acad. Sci. USA. Aug. 15, 2000, vol. 97, No. 17, pp. 9712-9717.*

Hardy, J. Amyloid, the Presenilins and Alzheimer's Disease. Trends in Neuroscience. 1997, vol. 20, No. 4, pp. 154-159.*

U.S. Appl. No. 60/271,092, filed Feb. 23, 2001.

U.S. Appl. No. 60/271,514, filed Feb. 26, 2001.

U.S. Appl. No. 60/293,762, filed May 25, 2001.

Acquati et al., "The gene encoding DRAP (BACE2), a glycosylated transmembrance protein of the aspartic protease family, maps to the Down critical region," *FEBS Letters* 468(1):59-64 (2000).

Altschul et al., "Basic Local Alignment Search Tool," *J. Mol. Biol.* 215:403-410 (1990).

Borchelt et al., "Accelerated Amyloid Deposition in the Brains of Transgenic Mice Coexpressing Mutant Presenilin 1 and Amyloid Precursor Proteins," *Neuron* 19:939-945 (1997).

Bradley et al., "Formation of germ-line chimaeras from embryo-derived teratocarcinoma cell lines." *Nature* 309:255-256 (1984).

De Strooper et al., "Deficiency of presenilin-1 inhibits the normal cleavage of amyloid precursor protein," *Nature* 391:387-390 (1998).

Farzan et al., "BACE2, a β-secretase homolog, cleaves at the β site and within the amyloid-β region of the amyloid-β precursor protein," *Proc. Nat'l. Acad. Sci.* 97(17):9712-9717 (2000).

Glenner & Wong, "Alzheimer's Disease and Down's Syndrome: Sharing of a Unique Cerebrovascular Amyloid Fibril Portein," *Biochemical and Biophysical Research Communications* 120:1131 (1984).

Hardy et al., "Amyloid, the presenilins and Alzheimer's disease," *TINS* 20:154-159 (1997).

Henikoff & Henikoff, "Amino acid substitution matrices from protein blocks," *Proc. Nat'l Acad. Sci. USA* 89:10915-10919 (1992).

Hsiao et al., "Correlative Memory Deficits, Aβ Elevation, and Amyloid Plaques in Transgenic Mice," *Science* 274:99-102 (1996).

Huber et al., "cDNA Cloning and Molecular Characterization of Human Brain Metalloprptease MP100: A β-Secretase Canadidate?" *Journal of Neurochemistry* 72:1215-1223 (1999).

Jaenisch et al., "Transgenic animals," *Science* 240:1468-1474 (1988).

Johnson-Wood et al., "Amyloid precursor protein processing and Aβ$_{42}$ deposition in a transgenic mouse model of Alzheimer disease," *Proc. Nat'l Acad. Sci. USA* 94:1550-1555 (1997).

Kang et al., "The Precursor of Alzheimer's Disease Amyloid A4 Protein Resembles a Cell-Surface Receptor," *Nature* 325:733-736 (1987).

Karlin & Altschul, "Applications and statistics for multiple high-scoring segments in molecular sequences," *Proc. Nat'l. Acad. Sci. USA* 90:5873-5787 (1993).

Kitaguchi et al., "Novel precursor of Alzheimer's disease amyloid protein shows protease inhibitory activity," *Nature* 331:530 (1988).

Lai et al., "Production of α-1,3-Galactosyltransferase Knockout Pigs by Nuclear Transfer Cloning," *Science* 295:1089-1092 (2002).

Needleman & Wunsch., "A General Method Applicable to the Search for Similarities in the Amino Acid Sequence of Two Proteins," *J. Mol. Biol.* 48:443 (1970).

Pearson & Lipman, "Improved tools for biological sequence comparison," *Proc. Nat'l Acad. Sci. USA* 85:2444-2448 (1988).

Ponte et al., "A New A4 Amyloid mRNA contains a domain homologous to serine proteinase inhibitors," *Nature* 331:525-527 (1988).

Roberds et al., "BACE knockout mice are healthy despite lacking the primary β-secretase activity in brain: implications for Alzheimer's disease therapeutics" *Human Molecular Genetics* 10:1317-1324 (2001).

Roger et al., "Behavioral and functional analysis of mouse phenotype: SHIRPA, a proposed protocol for comprehensive phenotype assessment," *Mamm. Genome* 8:711-713 (1997).

Selkoe et al., "Normal and Abnormal Biology of the β-Amyloid Precursor Protein," *Annual Rev. Neurosci* 17:489-517 (1994).

Sinha et al., "Cellular mechanisms of β-amyloid production and secretion," *Proc. Natl. Acad. Sci. USA* 96:11049-11053 (1999).

Sinha et al., "Purification and cloning of amyloid precursor protein β-secretase from human brain," *Nature* 402:537-540 (1999).

Smith & Waterman, "Comparison of Biosequences," *Adv. Appl. Math.* 2:482 (1981).

Sturchler-Pierrat et al., "Two amyloid precursor protein transgenic mouse models with Alzheimer disease-like pathology," *Proc. Nat'l. Acad. Sci. USA* 94:13287-13292 (1997).

Vassar et al., "β-Secretase Cleavage of Alzheimer's Amyloid Precursor Protein by the Transmembrane Aspartic Protease BACE," *Science* 286:735-741 (1999).

Wattler et al., "Construction of Gene Targeting Vectors from λKOS Genomic Libraries." *Biotechniques* 26:1150-1160 (1999).

Yan et al., "Membrane-anchored aspartyl protease with Alzheimer's disease β-secretase activity," *Nature* 402:533-537 (1999).

Cai et al., "Society for Neuroscience Abstracts", (2000) - vol. 26: Abstract No. 276.4.

Cai et al., "Nature Neuroscience", (2001) - vol. 4(3): pp. 233-234.

Citron, "Molecular Medicine Today", (2000) - vol. 6: pp. 392-397.

Hardy, Trends in Neurosciences, (1997) vol. 20(4), pp. 154-159.

Rodriguez et al., "Nature Genetic", (2000) - vol. 25: pp. 139-140.

Luo et al., "Nature Neuroscience", (2001) - vol. 4(3): pp. 231-232.

U.S. Appl. No 60/271,092, filed Feb. 23, 2001, Gurney.

U.S. Appl. No. 60/271,514, filed Feb. 26, 2001, McConlogue.

U.S. Appl. No. 60/293,762, filed May 25, 2001, Gurney.

* cited by examiner

SEQUENCE LISTING

```
<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: PCR primer for probe B.

<400> SEQUENCE: 1
gacagatgaa ttcctatctt g                                              21
```

```
<210> SEQ ID NO 2
<211> LENGTH: 21
<212> TYPE: DNA
<213> ORGANISM: Artificial Sequence
<220> FEATURE:
<223> OTHER INFORMATION: PCR primer for probe B.

<400> SEQUENCE: 2
gtctcttcct catcaactgt c                                              21

<210> SEQ ID NO 3
<211> LENGTH: 21
<212> TYPE: DNA
<213> ORGANISM: Artificial Sequence
<220> FEATURE:
<223> OTHER INFORMATION: PCR primer for probe P.

<400> SEQUENCE: 3
cggagcccaa ctgtcaaaaa g                                              21

<210> SEQ ID NO 4
<211> LENGTH: 18
<212> TYPE: DNA
<213> ORGANISM: Artificial Sequence
<220> FEATURE:
<223> OTHER INFORMATION: PCR primer for probe P.

<400> SEQUENCE: 4
ccaaccgtgc cctcctgc                                                  18

<210> SEQ ID NO 5
<211> LENGTH: 20
<212> TYPE: DNA
<213> ORGANISM: Artificial Sequence
<220> FEATURE:
<223> OTHER INFORMATION: PCR primer for hybridization probe

<400> SEQUENCE: 5
gtgtcatgta actcaggctg                                                20

<210> SEQ ID NO 6
<211> LENGTH: 22
<212> TYPE: DNA
<213> ORGANISM: Artificial Sequence
<220> FEATURE:
<223> OTHER INFORMATION: PCR primer for hybridization probe.

<400> SEQUENCE: 6
ggtaatctat gcagagcact tg                                             22

<210> SEQ ID NO 7
<211> LENGTH: 42
<212> TYPE: PRT
<213> ORGANISM: Homo sapiens
<220> FEATURE:
<223> OTHER INFORMATION: A-beta 42 sequence.

<400> SEQUENCE: 7

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40
```

US 7,309,811 B2

TRANSGENIC MICE KNOCKOUTS OF BACE-1

CROSS-REFERENCES TO RELATED APPLICATIONS

This application derives priority from U.S. Ser. No. 60/271,092 filed Feb. 23, 2001, U.S. Ser. No. 60/271,514 filed Feb. 26, 2001 and U.S. Ser. No. 60/293,762, filed May 25, 2001, each of which is incorporated by reference for all purposes.

TECHNICAL FIELD

The invention resides in the technical fields of neurological diseases and medicine.

BACKGROUND OF THE INVENTION

Alzheimer's Disease (AD) represents one of the great unsolved medical needs confronting society during this millennium. Despite considerable work during the past quarter century, no medicines exist that attack the underlying pathophysiology of the disease. One of the cardinal features of AD is deposition of plaques comprised of aggregated beta-amyloid peptides (Aβ) in the brain, particularly in regions associated with cognition and memory. Selkoe, *Annu. Rev. Neurosci.*, 17, 489–517 (1994). Overproduction of Aβ, which appears to be directly neurotoxic, can be detected at the earliest stages of AD and, in fact, before cognitive dysfunction is detectable. Aβ is produced from its precursor protein, APP, by proteolytic processing at its N and C termini by β-and γ-secretase enzymes, respectively. Mutations in APP, presenilin-1, or presenilin-2 genes result in over-production of Aβ1-42 peptide and cause early onset, familial AD. The identity of the β-and γ-secretases have been studied since 1984, and in 1999 the elusive N-terminal β-site APP cleaving enzyme (BACE-1) was reported. Yan, et al., *Nature*, 402, 533–537 (1999). It remains possible that there are additional proteases with β-secretase activity.

BACE-1 mRNA is expressed widely at low levels, in the brain at moderate levels and in the pancreas at higher levels. However, β-secretase activity is low in pancreas and highest in brain. This discrepancy between mRNA and activity is probably due to a splice variant lacking two-thirds of exon 3 being the predominant BACE-1 transcript in pancreas, resulting in a protein that is incompletely processed and retained in the endoplasmic reticulum. In the brain, BACE-1 mRNA is widely expressed only in neurons, with most pronounced expression in the cerebellum, cortex, and hippocampus observed by in situ hybridization. BACE-1 is co-localized with its substrate, APP, in the trans-Golgi network of cells.

Because small-molecule BACE-1 inhibitors are being studied as potential Alzheimer's disease pharmacotherapeutics, it is necessary to prove that BACE-1 is the primary β-secretase of brain and to understand what effects BACE-1 inhibitors may have beyond inhibition of APP processing. It is also important to show that BACE-1 comprises the major β-secretase activity in brain. This disclosure reports and claims those findings and inter alia their use in methods of screening.

BRIEF DESCRIPTION OF THE FIGURES

FIG. 1A. Three frt sites (gray triangles) and a neomycin-resistance gene were appropriately integrated into ES cells.

FIG. 1B. Two Southern blots on left showing that mice produced using targeted ES cells also contained the targeted allele. After crossing targeted BACE-1 heterozygote mice with a transgenic mouse expressing flp recombinase under the control of a CMV enhancer/chicken actin promoter, exons 4–8 had been deleted in heterozygous offspring as demonstrated by the Southern blot on right.

FIG. 1C. Generation of BACE-1 knockout mice with deletion and insertion in exon 1. The portion of the BACE-1 genomic locus containing exon 1 is shown with the position of exon 1 (solid box) underlined and labeled and the position of the initiating methionine indicated by ATG. The region which is replaced by the expression cassette is underlined and labeled delta KO. The structure of the knockout locus is shown below with the inserted expression cassette shown by the striped box. IRES indicates the internal ribosomal entry site for polycistronic translation. βGAL indicates the β-galactosidase gene, MC1 NEO indicates an expression cassette expressing the neomycin resistance gene driven by the polyoma enhancer/herpes simplex virus thymidine kinase promoter.

FIG. 2A. β-secretase activity was measured in cell extracts from +/+ (WT, open circles) and −/− (KO, open triangles) primary cortical cultures and is shown as a function of cellular protein added to the reaction.

FIGS. 2B and 2C. β-secretase activity in 2.3 micrograms of protein from cell extracts, FIG. 2B; and Aβx-40 released into the medium after 3 days of collection, FIG. 2C; are shown from individual +/+ (WT) and −/− (KO) fetuses. Aβx-40 measurements collected from multiple wells were normalized to mg of cellular protein in the well. Error bars indicate standard deviations.

FIG. 3A. The statine-based substrate analogue β-secretase inhibitors P10-P4' statV (I1, circle and diamond) and P10-P4' stat (I2, square and triangle) were used to inhibit β-secretase activity from wildtype P2 pellets (closed diamond and triangle) and from BACE-1 purified from human brain (open circle and square). I1 has an IC50 of 2 nM, and I2 has an IC50 of 200 µM for. both purified BACE-1 and P2 pellets.

FIG. 3B. β-secretase activity measured in brain homogenates from homozygous and heterozygous exon 1-disrupted BACE-1 knockout mice. Cortexes from four +/+ and four −/− mice were homogenized and β-secretase activity measured in P2 pellets as described in methods. Activity per mg of P2 membrane protein is shown. Activity from the −/− samples are below the limits of detection of the assay. Error bars indicate standard deviations.

BRIEF SUMMARY OF THE INVENTION

Figure 1A:
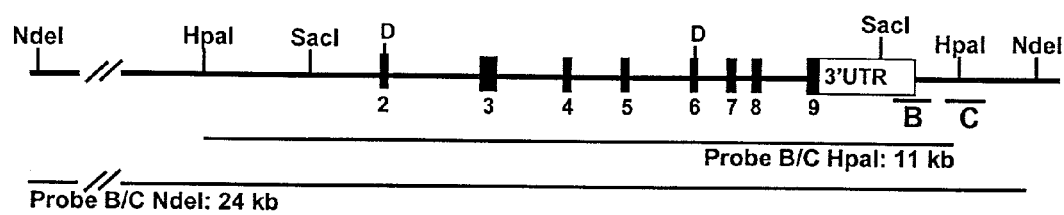
FIGS. 1A, 1B and 1C. Generation and genotyping of BACE-1 knockout mice lacking exons 4–8.
Figure 1A:
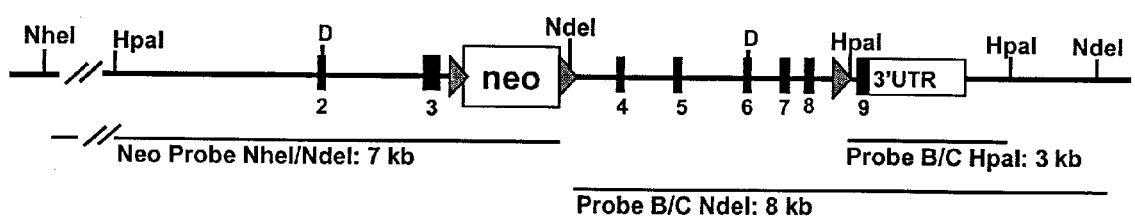
Figure 1A:
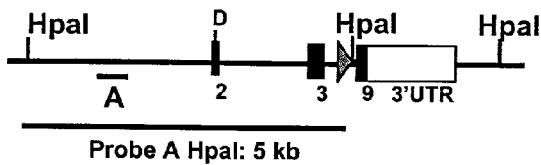
Figure 1B:
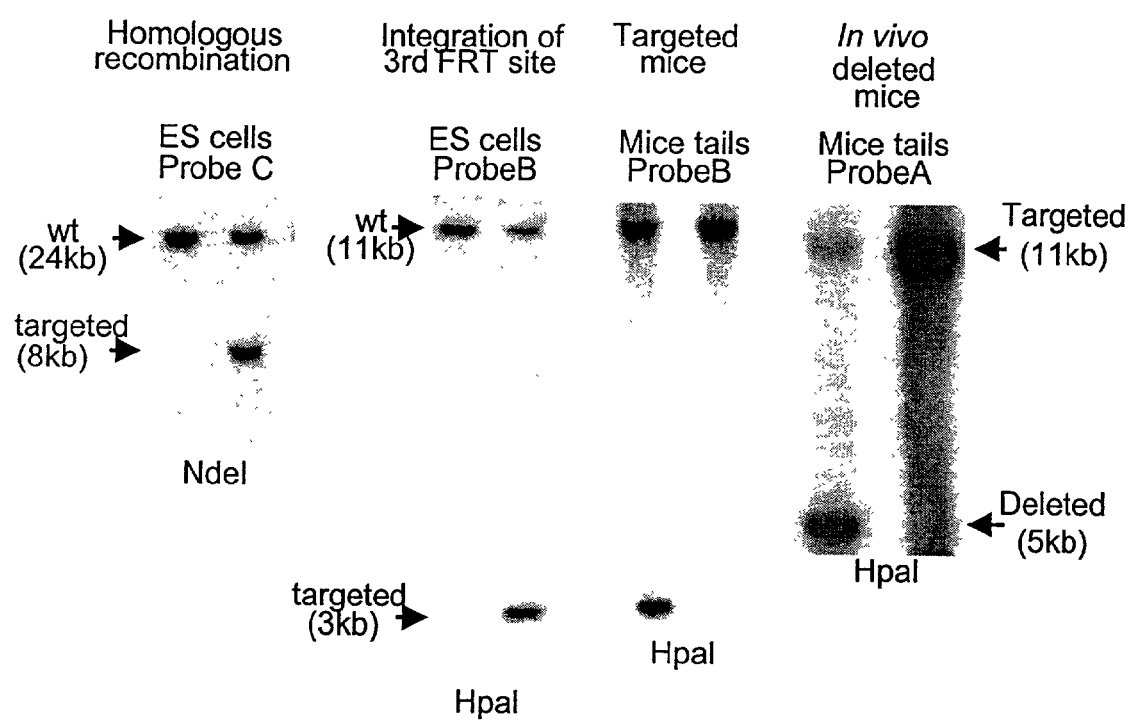

The invention provides a transgenic nonhuman animal comprising at least one nonfunctional allele of a betasecretase-1 (BACE-1) gene. Some transgenic animals are homozygous for the allele. Some transgenic animals are rodents, such as mice or rats.

Some transgenic animals are produced by homologous recombination between an endogenous allele of the gene and a construct containing a positive selection marker flanked by segments showing sufficient sequence relatedness to the gene for the construct to recombine with the endogenous allele introducing the positive selection marker into the endogenous allele and rendering it nonfunctional. Other transgenic animals are produced by homologous recombination between an endogenous allele of the gene and a construct containing a positive selection marker flanked by segments showing sufficient sequence relatedness to the gene to undergo homologous recombination with it, these segments being flanked by frt recombination sites, whereby the construct recombines with the endogenous gene introducing the positive selection marker and frt recombination sites into the endogenous allele, and the frt recombination sites undergo recombination with each other thereby excising DNA between the flp recombination sites resulting in a deleted nonfunctional form of the endogenous allele.

In some transgenic animals, the allele is rendered nonfunctional by deletion of at least a segment of an exon of the gene. In some transgenic animals, the allele is rendered nonfunctional by deletion of at least a segment from exon 1 of the gene. In some transgenic animals, the allele is rendered nonfunctional by homologous recombination with a targeting vector comprising a lambda KOS genomic clone of BACE-1. In some such animals, the lambda KOS genomic clone comprises a BACE-1 nucleic acid from murine strain 129/SvEv covering 5.5 kb upstream and 2 kb downstream of exon 1. In some animals, the allele is rendered nonfunctional by a 165 base pair deletion of exon 1 starting from 2 basepairs past the initiating methionine and extending through the end of exon 1 replaced with an expression cassette in the targeting vector electroporated into 129 ES cells used to generate the transgenic nonhuman animal. In some animals, the allele is rendered nonfunctional by deletion of exons 4–8.

Some transgenic animals further comprise a transgene comprising a mutation in the APP gene associated with familial Alzheimer's disease. In some such animals, the transgene comprises a mutation at codons 595 and 596 of human APP695, or an isoform or fragment thereof, wherein the amino acid residues at positions corresponding to positions 595 and 596 are asparagine and leucine, respectively. In some such animals, the transgene comprises a mutation at codon 717 of APP770 or an isoform or fragment of APP770 having a mutant amino acid residue at position 717. In some such animals, the mutant amino acid residue is isoleucine, phenylalanine or glycine. In some such animals, the animal is homozygous for the non-functional allele. In some such animals, the animal is heterozygous for the transgene.

The invention further provides a cortical cell culture derived from the transgenic animal of claim 1. The cortical cell culture can be a primary cell culture. 21. Some such cortical cell cultures comprises a detectable amount of a peptide recognized by an antibody that recognizes residues 13–28 of Aβ.

The invention further provides methods for screening for an inhibitor of the production by a protease other than beta-secretase ("non-beta-secretase protease") of a peptide recognized by an antibody that recognizes residues 13–28 of Aβ. Such methods comprise: exposing a transgenic animal as described above or a cortical cell culture derived therefrom to an agent, and detecting the peptide produced in the transgenic animal or cell culture exposed to the agent, wherein a reduced amount of peptide produced in the exposed transgenic animal or cell culture relative to a transgenic animal or cell culture which has not been exposed to the agent is indicative of inhibitory activity.

The invention further provides methods of analyzing potential side-effects for an inhibitor of beta-secretase. Such methods comprise exposing a transgenic animal as described above or a cortical cell culture derived therefrom to an inhibitor of beta secretase; measuring whether there is a change in the level of at least one component of the transgenic animal or cortical cell responsive to the administration of the inhibitor; wherein a change in the level of at least one component indicates a potential side effect. The measuring step can measure changes in the levels of a plurality of mRNA species.

The invention further provides an embryonic stell cell comprising at least one nonfunctional allele of a beta-secretase-1 (BACE-1) gene. Some embryonic stem cells are homozygous for the allele. Some embryonic stem cells are mouse embryonic stem cells. Some embryonic stem cells are produced by homologous recombination with a targeting vector designed in a way that, upon homologous recombination, exons 4 to 8 of the BACE-1 gene are flanked with FLP recombinase target sites (frt sites). Some embryonic stem cells are produced by homologous recombination with a targeting vector designed in a way that, with respect to the genomic locus, the 5' region of homology covered 4.5 kb and the 3' region 4.3 kb until the third frt site, and an additional 1.5 kb further 3'. Some embryonic stem cells are homozygous for a nonfunctional allele lacking exons 4–8 of BACE-1. Some embryonic stem cells are produced by homologous recombination with a first targeting vector that introduces a neomycin resistance gene in the BACE-1 gene and with a second targeting vector that replaces the neomycine resistance gene with a hygromycin resistance gene cassette.

The invention further provides a blastocyst formed by differentiation of an embryonic stem cell as described above.

DEFINITIONS AND ABBREVIATIONS

Abbreviations

Aβ, beta-amyloid peptide; AD, Alzheimer's disease; APP, amyloid precursor protein; BACE-1, Beta-site APP-cleaving enzyme.

Definitions $APP^{695}$, $APP^{751}$, and $APP^{770}$ refer, respectively, to the 695, 751, and 770 amino acid residue long polypeptides encoded by the human APP gene. See Kang et al., *Nature* 325, 773 (1987); Ponte et al., *Nature* 331, 525 (1988); and Kitaguchi et al., *Nature* 331, 530 (1988). Different numbering conventions are used for the different isoforms; however, these are readily interconverted. Amino acids within the human amyloid precursor protein (APP) are assigned numbers according to the sequence of the APP770 isoform unless otherwise stated.

Aβ, also known as β-amyloid peptide, or A4 peptide (see U.S. Pat. No. 4,666,829; Glenner & Wong, *Biochem. Biophys. Res. Commun.* 120, 1131 (1984)), is a peptide of 39–43 amino acids, which is the principal component of characteristic plaques of Alzheimer's disease. Aβ is generated by processing of a larger protein APP by two enzymes, termed β and γ secretases (see Hardy, *TINS* 20, 154 (1997)). Known mutations in APP associated with Alzheimer's disease occur proximate to the site of β or γ secretase, or within Aβ. For example, position 717 is proximate to the site of γ-secretase cleavage of APP in its processing to Aβ, and positions 670/671 are proximate to the site of β-secretase cleavage. It is believed that the mutations cause AD by interacting with the cleavage reactions by which Aβ is formed so as to increase the amount of the 42/43 amino acid form of Aβ generated.

Aβ has the unusual property that it can fix and activate both classical and alternate complement cascades. In particular, it binds to Clq and ultimately to C3bi. This association facilitates binding to macrophages leading to activation of B cells. In addition, C3bi breaks down further and then binds to CR2 on B cells in a T cell dependent manner leading to a 10,000 increase in activation of these cells. This mechanism causes Aβ to generate an immune response in excess of that of other antigens.

Aβ has several natural occurring forms. The human forms of Aβ are referred to as Aβ39, Aβ40, Aβ41, Aβ42 and Aβ43. The sequences of these peptides and their relationship to the APP precursor are illustrated by FIG. 1 of Hardy et al., TINS 20, 155–158 (1997). For example, Aβ42 has the sequence:

H2N-Asp-Ala-Glu-Phe-Arg-His-Asp-Ser-Gly-Tyr-Glu-Val-His-His-Gln-Lys -Leu-Val-Phe-Phe-Ala-Glu-Asp-Val-Gly-Ser-Asn-Lys-Gly-Ala-Ile-Ile-Gly-Leu-Met-Val-Gly -Gly-Val-Val-Ile-Ala-OH.

Aβ41, Aβ40 and Aβ39 differ from Aβ42 by the omission of Ala, Ala-Ile, and Ala-Ile-Val respectively from the C-terminal end. Aβ43 differs from Aβ42 by the presence of a threonine residue at the C-terminus.

An exogenous DNA segment is one heterologous to the cell (e.g., from a different species than the cell), or homologous to a DNA segment of the cell but in an unnatural position in the host cell genome. Conversely, an endogenous DNA segment or gene is one naturally occurring in a species and occupying its natural positions.

In a transgenic mammal, all, or substantially all (i.e., with the possible exception of a few reversions by somatic mutations), of the germline and somatic cells contain a transgene introduced into the mammal or an ancestor of the mammal at an early embryonic stage.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

DETAILED DESCRIPTION OF THE INVENTION

I. General

The invention provides an animal deficient in a functional allele encoding a functional enzyme with the ability to cleave β-amyloid precursor protein ("APP") between amino acids 596 and 597 ("beta-secretase") (numbered by the APP695 convention). Preferably, the animal has been engineered to be lacking at least one allele for a gene encoding a functional beta-secretase, or an offspring of the animal lacking said functional beta-secretase allele (both of which are referred to herein as "beta-secretase knock-out").

The invention also provides a beta-secretase knock-out comprising a transgene comprising a mutation in the APP gene associated with familial Alzheimer's disease.

The invention also provides a method for screening for agents that inhibit proteases other than beta-secretase that are implicated in the production of Aβ or fragments thereof ("non-beta-secretase proteases"). Such proteases include, but are not limited to, the putative gamma-secretase, presenilin-1, presenilin-2, and BACE-2.

In addition to being useful for screening for agents that inhibit non-beta-secretase proteases, the animals are also useful to identify additional targets for intervention and to assess the likelihood of toxicity in animals of various ages of agents that inhibit beta-secretase.

II. Beta-secretase

A beta-secretase enzyme cleaves amyloid precursor protein (APP) between residues 596 and 597 (APP695 numbering convention) or 670 and 671 (APP770 numbering convention). Human and mouse forms of this enzyme has been cloned by a number of groups and reported to be a membrane-bound aspartyl protease. (Sinha, *Nature* 402: 537–540, 1999; Yan, *Nature* 402:533–536, 1999; Vassar, *Science*, 286:735–741, 1999.) The sequences reported in these publications are alleles of the same gene, referred to herein as BACE-1. Unless otherwise apparent from the context, reference to a beta-secretase enzyme, cDNA or gene refers to the BACE-1 form, as described in any of the above publications, as well as allelic, species and induced variants thereof. Induced variants preferably show at least 90%, 95% or 99% sequence identity at the nucleic acid or amino acid level to at least one of the exemplary BACE-1 sequences described in the above pucliations. A second nonallelic form of beta-secretase has been described by Pharmacia WO 00/17369 published 30 Mar. 2000; *FEBS Lett* Feb. 18, 2000;468(1):59–64; and Acquati et al., *Proc Natl Acad Sci USA*. Aug. 15, 2000; 97(17):9712–7. This form will be referred to as BACE-2.

III. Generation of Transgenic Animals

Transgenic animals of the invention have one or both endogenous alleles of the BACE-1 gene in nonfunctional form. Inactivation can be achieved by modification of the endogenous gene, usually, a deletion, substitution or addition to a coding region of the gene. The modification can prevent synthesis of a gene product or can result in a gene product lacking functional activity. Typical modifications are the introduction of an exogenous segment, such as a selection marker, within an exon thereby disrupting the exon or the deletion of an exon.

Inactivation of endogenous genes in mice can be achieved by homologous recombination between an endogenous gene in a mouse embryonic stem (ES) cell and a targeting construct. Typically, the targeting construct contains a positive selection marker flanked by segments of the gene to be targeted. Usually the segments are from the same species as the gene to be targeted (e.g., mouse). However, the segments can be obtained from another species, such as human, provided they have sufficient sequence identity with the gene to be targeted to undergo homologous recombination with it. Typically, the construct also contains a negative selection marker positioned outside one or both of the segments designed to undergo homologous recombination with the endogenous gene (see U.S. Pat. No. 6,204,061). Optionally, the construct also contains a pair of site-specific recombination sites, such as frt, position within or at the ends of the segments designed to undergo homologous recombination with the endogenous gene. The construct is introduced into ES cells, usually by electroporation, and undergoes homologous recombination with the endogenous gene introducing the positive selection marker and parts of the flanking segments (and frt sites, if present) into the endogenous gene. ES cells having undergone the desired recombination can be selected by positive and negative selection. Positive selection selects for cells that have undergone the desired homologous recombination, and negative selection selects against cells that have undergone negative recombination. These cells are obtained from preimplantation embryos cultured in vitro. Bradley et al., *Nature* 309, 255–258 (1984) (incorporated by reference in its entirety for all purposes). Transformed ES cells are combined with blastocysts from a non-human animal. The ES cells colonize the embryo and in some embryos form or contribute to the germline of the resulting chimeric animal. See Jaenisch, *Science*, 240, 1468–1474 (1988) (incorporated by reference in its entirety for all purposes). Chimeric animals can be bred with nontransgenic animals to generate heterozygous transgenic animals. Heterozygous animals can be bred with each other to generate homozygous animals. Either heterozygous or homozygous animals can be bred with a transgenic animal expressing the flp recombinase. Expression of the recombinase results in excision of the portion of DNA between introduced frt sites, if present.

Functional inactivation can also be achieved for other species, such as rats, rabbits and other rodents, bovines such as sheep, caprines such as goats, porcines such as pigs, and bovines such as cattle and buffalo, are suitable. For animals other than mice, nuclear transfer technology is preferred for generating functionally inactivated genes. See Lai et al., *Sciences* 295, 1089–92 (2002). Various types of cells can be employed as donors for nuclei to be transferred into oocytes, including ES cells and fetal fibrocytes. Donor nuclei are obtained from cells cultured in vitro into which a construct has been introduced and undergone homologous recombination with an endogenous gene, as described above (see WO 98/37183 and WO 98/39416, each incorporated by reference in their entirety for all purposes). Donor nuclei are introduced into oocytes by means of fusion, induced electrically or chemically (see any one of WO 97/07669, WO 98/30683 and WO 98/39416), or by microinjection (see WO 99/37143, incorporated by reference in its entirety for all purposes). Transplanted oocytes are subsequently cultured to develop into embryos which are subsequently implanted in the oviducts of pseudopregnant female animals, resulting in birth of transgenic offspring (see any one of WO 97/07669, WO 98/30683 and WO 98/39416). Transgenic animals bearing heterozygous transgenes can be bred with each other to generate transgenic animals bearing homozygous transgenes.

Some transgenic animals of the invention have both an inactivation of one or both alleles of BACE-1 and a second transgene that confers an additional phenotype related to Alzheimer's, disease, its pathology or underlying biochemical processes. For example, some transgenic animals have an inactivation of one or both alleles of BACE-1 and a second transgene encoding a variant form of APP, in which the variation is associated with familial Alzheimer's disease. Such animals can be produced by breeding a transgenic animal with a functional inactivation of BACE-1 with a transgenic animal expressing a mutated form of human APP. Examples of the latter include mice bearing a 717 mutation of APP described by Games et al., *Nature* 373. 523–527, and mice bearing a Swedish mutation of APP such as described by McConlogue et al., U.S. Pat. No. 5,612,486 and Hsiao et al., *Science* 274, 99 (1996); Staufenbiel et al., *Proc. Natl. Acad. Sci. USA* 94, 13287–13292 (1997); Sturchler-Pierrat et al., *Proc. Natl. Acad. Sci. USA* 94, 13287–13292 (1997); Borchelt et al., *Neuron* 19, 939–945 (1997)). The 717 mutation of APP can be phenylalanine, glycine or isoleucine.

IV. Methods of Screening

The transgenic animals of the invention, or cells derived therefrom, are useful for various methods of screening compounds. In some methods, the transgenic animals are used to screen compounds to identify inhibitors of enzymes having beta-secretase activity other than BACE-1. Beta-secretase cleavage generates two products referred to as ATF-APP and Aβ. The cleavage reaction and inhibition thereof can thus be monitored from the appearance of either of these fragments. Appearance of ATF-APP can be monitored as described by McConlogue et al., U.S. Pat. No. 5,612,486 and Aβ as described in the present examples or U.S. Pat. No. 6,114,133. Inhibition of a compound is determined by comparing the level of ATF-APP or Aβ in the presence or absence of the compound. Reduction in the level of ATF-APP or Aβ in the presence relative to the absence of compound signals that the compound is an inhibitor of beta-secretase activity. Compounds that are inhibitors of beta-secretase activity have a pharmacological activity that is potentially useful in treating Alzheimer's disease and can be subjected to further screening. The transgenic animals of the invention are also useful for screening for inhibitors of other proteolytic enzymes that act on APP including gamma secretase, and possibly presenilins 1 and 2. Gamma secretase generates the C-terminus of Aβ and its cleavage can be monitored by following generation of Aβ peptide or epitopes thereof Antibodies for detecting different epitopes in Aβ are described in WO00/72880.

The transgenic animals of the invention or cortical cells derived therefrom are also useful for determining a toxicity profile of compounds that are known to be inhibitors of beta-secretase (e.g., as a result of previous screening in a mouse model such as Games et al., supra, having the beta-secretase function). The toxicity profile can be determined by monitoring expression of a large number of mRNAs or proteins encoded thereby. Arrays for expression monitoring and equipment and procedures for using them are available from Affymetrix. The expression profile of an inhibitor under test can be compared with profiles of other compounds that are known to have or not have undesired side effects (see U.S. Pat. Nos. 5,811,231; 6,040,138). Similarity of profile with one or more compounds not prone to side effects signals that an inhibitor is not likely to have side effects itself, and thus remains a candidate for further screening (e.g., in clinical trials). Similarity of profile with one or more compounds having side effects signals that an inhibitor may itself be prone to side effects. Because these side effects do not arise as a result of the inhibitor's interaction with beta-secretase, it may be possible to redesign an inhibitor such that it retains its beta secretase inhibitory characteristics but loses the undesired side effects. BACE-1 knockout animals are also useful to distinguish potential mechanisms of action and evaluate structure activity relationships of pharmacological agents with potential activity in treating Alzheimer's disease.

The transgenic animals of the invention or cortical cells derived therefrom can also be used as control for purposes of comparison with transgenic animal models of Alzheimer's disease that have functional BACE-1. An inhibitor of BACE-1 should inhibit production of Aβ or ATF-APP in a transgenic animal model having BACE-1 function but should have no effect in transgenic animals that have both alleles of BACE-1 functionally inactivated.

EXPERIMENTAL

This invention discloses two lines of BACE-1 knockout mice: one by replacing a part of exon 1 and another by deleting exons 4–8 (FIG. 1A). The exon 1 disruption contained an inserted expression cassette immediately downstream from the initiating methionine, and the exon 4–8 deletion removed one of the two aspartate residues at the active site. Deletion of one or both alleles of the BACE-1 gene conveyed no developmental disadvantage, as the genotypes were transmitted in numbers approximating those expected for Mendelian inheritance. Specifically, genotyped offspring from heterozygote X heterozygote crosses to date of mice from the two lines are as follows: wild-type: heterozygous:homozygous=29:77:29 (the offspring within each of the two lines also roughly followed Mendelian genetics although the number of offspring bred from the exon 4–8 line is still relatively small). Necropsy was performed on exon 1-disrupted and exon 4–8-deleted BACE-1 −/−, +/−, and +/+ mice to examine tissues for gross pathological changes (Table 1). No gross abnormalities clearly related to genotype were noted at any age. Terminal body weight and weights of brain, kidney, adrenals, thymus, liver, pancreas, testes, and ovaries did not differ among the genotypes. In general, few gross or microscopic differences between BACE-1 −/−, +/−, and +/+ mice were observed. In particular, the morphology of the brain was normal.

BACE-1-deficient animals weaned and thrived normally as compared to their wild-type and heterozygous littermates. Animals were repeatedly observed in their home cages for gross behavioral abnormalities, and none was noted. Urine was collected over a 24-hour period on four consecutive days from ten animals of each genotype, aged 7–17 weeks. No differences in standard urinalysis endpoints including urinary volume, pH, specific gravity, urinary sediment, urine glucose and protein levels were found among any of the genotypes. Also, no genotype-related differences in a standard battery of clinical chemistry parameters including BUN, creatinine, glucose, transaminases, bilirubin, electrolytes, creatine kinase, and alkaline phosphatase were detected in these animals. Cellular composition of blood was indistinguishable between homozygous knockout, heterozygous, and wild-type littermates.

Male and female mice lacking exon 1 of the BACE-1 gene were tested on several measures of physiological function, as well as basal behavior and reactivity. Ten wild type (+/+), ten heterozygous (+/−) and ten homozygous (−/+) mice ranging from 50–120 days of age (Table 1) were used for these tests. Age was balanced across sex and genotype, except the female −/− mice (n=2, both at the upper end of the range). Gross behavioral observations and scoring for physical and physiological function were done as per an amended version of the "SHIRPA" test. See. Roger et al., *Mamm. Genome*, 8, 711–713 (1997) and open field activity was measured in photocell-equipped activity monitors. Although these results must be regarded as preliminary until larger numbers of mice are tested at various ages, we found no obvious differences observed between the genotypes.

Figure 2A:
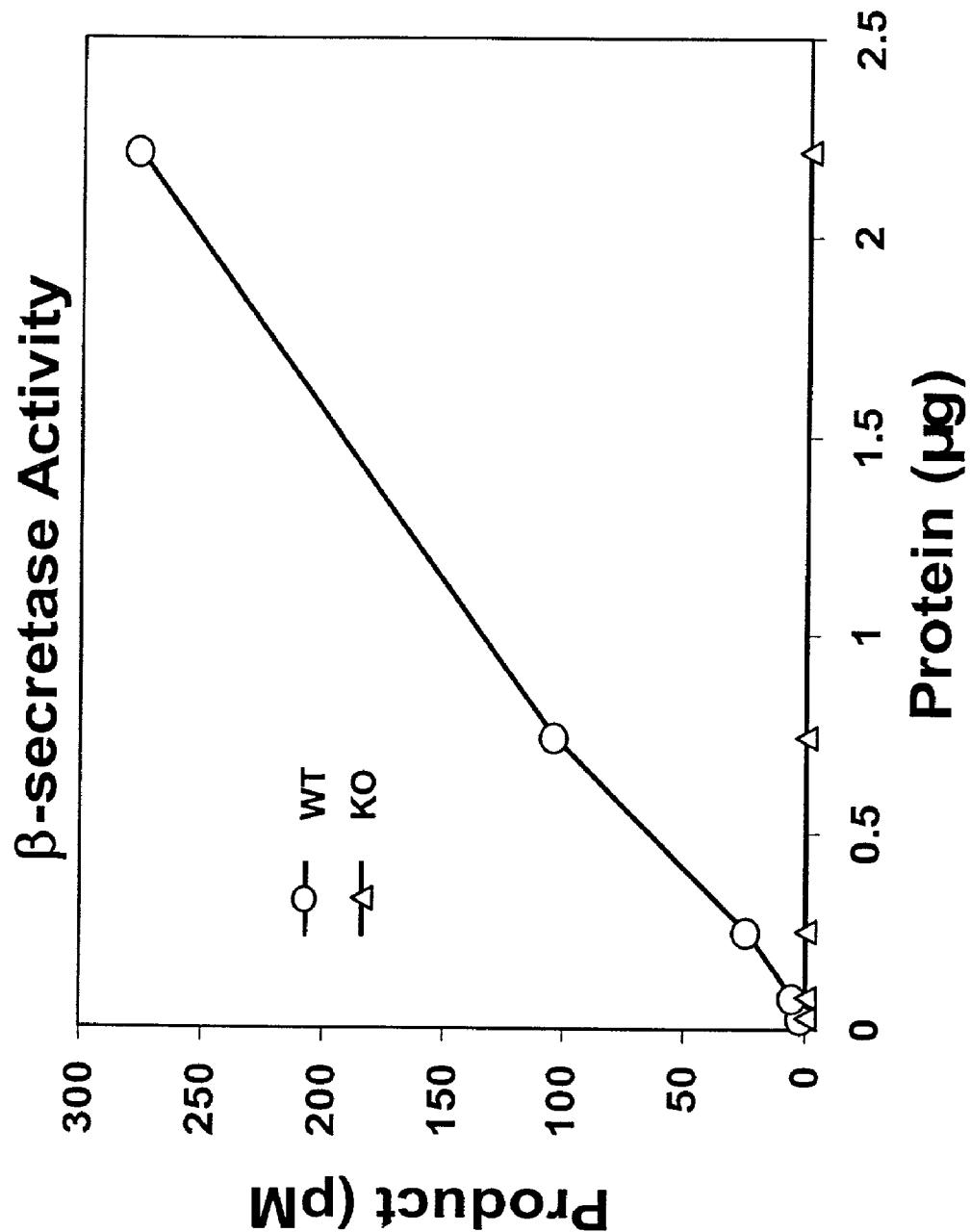
FIGS. 2A, 2B, and 2C. β-secretase activity and Aβ production in primary cortical cells from wild type and homozygous BACE-1 knockout mice. Primary cortical cultures were generated from individual −/− and +/+ fetuses generated from crossing male and female −/+ exon 1-disrupted BACE-1 knockout mice. Five days after plating, the medium was exchanged and 2 days later cells were harvested. Medium was also harvested on days 1, 2 and 3 after the medium exchange.
Figure 2B:
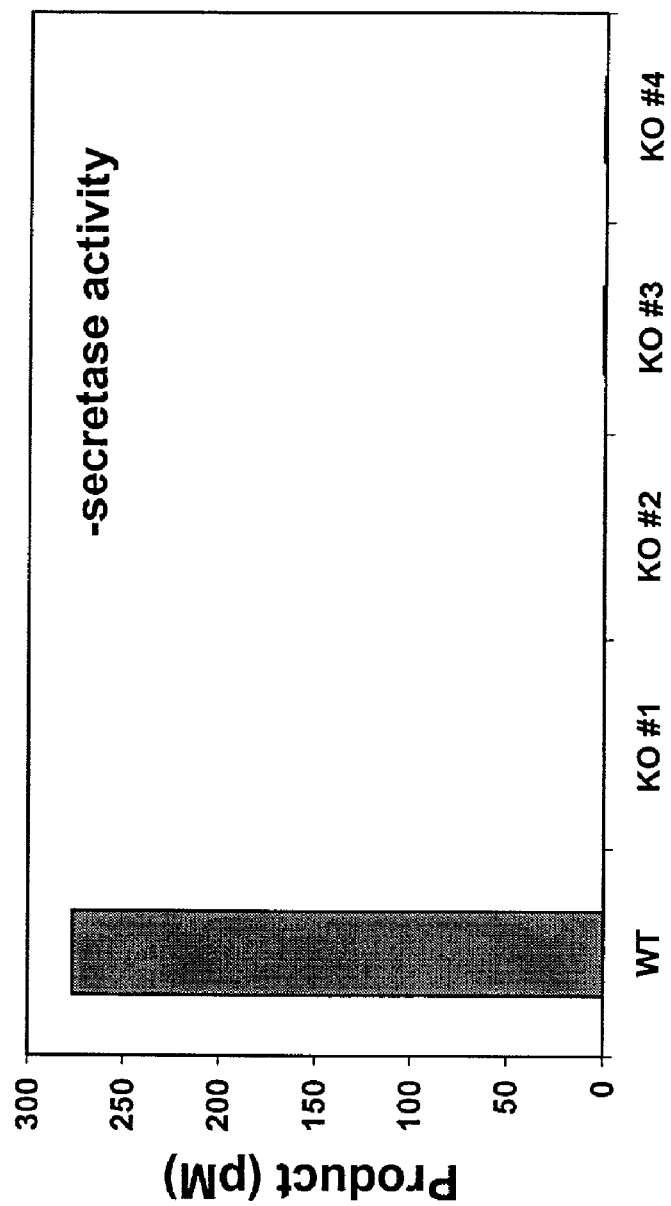
Figure 2C:
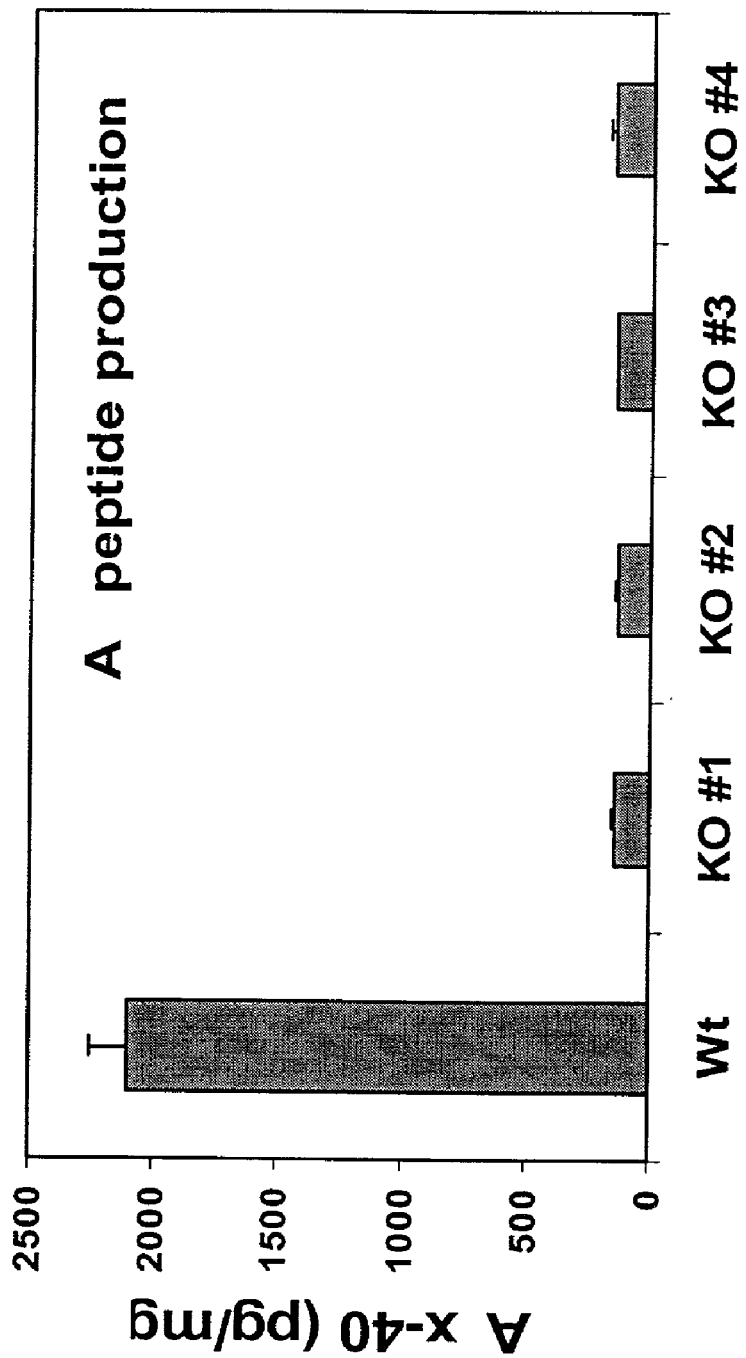

All mice showed normal gait, with normal exploratory behavior including sniffing, rearing, urination and defecation. The exploratory phase was followed by habituation, which also was similar for all groups. There were no differences in grip strength and all mice had a strong righting reflex with a normal reaction to being touched along their dorsal surface. The geotaxis response, measured as the time to turn 180°, and begin to ascend a vertical screen, was very quick, and the same for all groups. All genotypes had eyes that were completely open on arousal, with a similar blink response to a light touch to the cornea. None of the animals showed body tremor or piloerection, and the resting respiration and body temperature did not differ between the groups. Likewise, all genotypes showed a similar pinna reflex distribution in response to a light touch to the inside of the ear.

β-secretase was originally defined operationally as the activity generating a specific cleavage in APP to release the N-terminus of Aβ and an intact secreted fragment sAPPβ. Although BACE-1 has been identified as a protease with such activity, it is not known whether BACE-1 is the only, or even the primary, β-secretase in brain cells. To determine the degree to which BACE-1 disruption decreased β-secretase activity, enzyme activity was measured in primary cortical cultures from −/−, −/+, and +/+ fetuses. β-secretase activity from wildtype cultures was linear with amount of cellular protein added. No β-secretase activity was detected in primary cortical cultures from homozygous BACE-1 knockout animals. However, activity measured in wild-type cortical cultures showed activity above background even when diluted 27-fold. Therefore BACE-1 is the primary β-secretase in cortical cells. See FIGS. 2A, 2B and 2C.

If BACE-1 is functioning in intact cells as β-secretase, one would predict that Aβ levels would be reduced in BACE-1 knockout cultures. To measure BACE-1 effects on APP processing in brain cells, Aβx-40 was measured in primary cortical cultures used for β-secretase activity described above. Since the ELISA for Aβx-40 readily detects rodent Aβ, it was used instead of other Aβ ELISAs. In knockout −/− cultures Aβx-40 production was reduced 15-fold relative to wild-type cultures. These decreases in Aβ peptide production are consistent with results from other BACE-1 knockout mice recently reported. Furthermore, this finding is consistent with the amount of β-secretase activity we measured in these cultures. Therefore, BACE-1 is the major β-secretase in cortical neurons and is required for A β production.

Figure 3A:
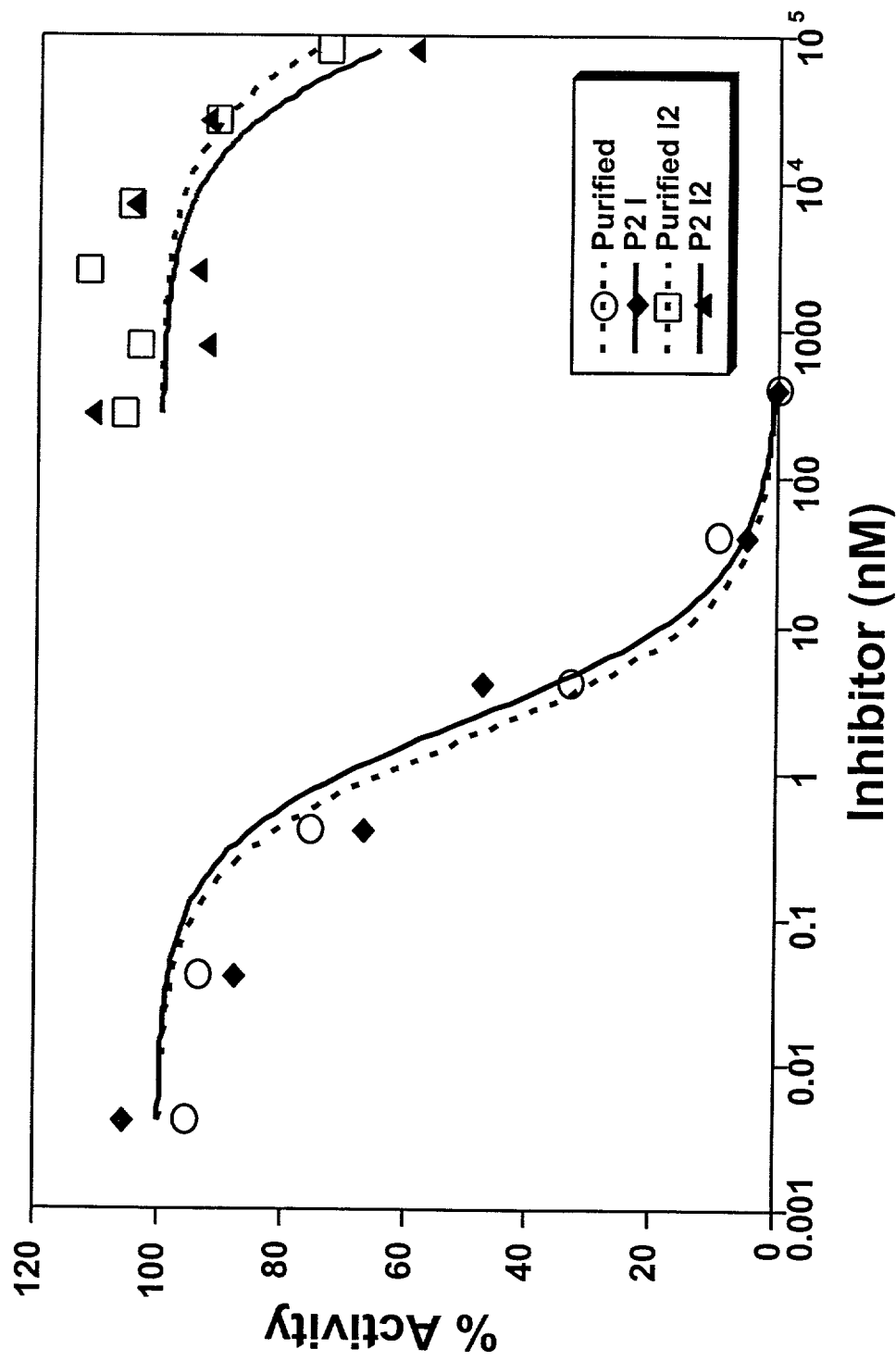
FIGS. 3A and 3B. β-secretase activity and inhibition in brain from BACE-1 knockout mice.
Figure 3B:
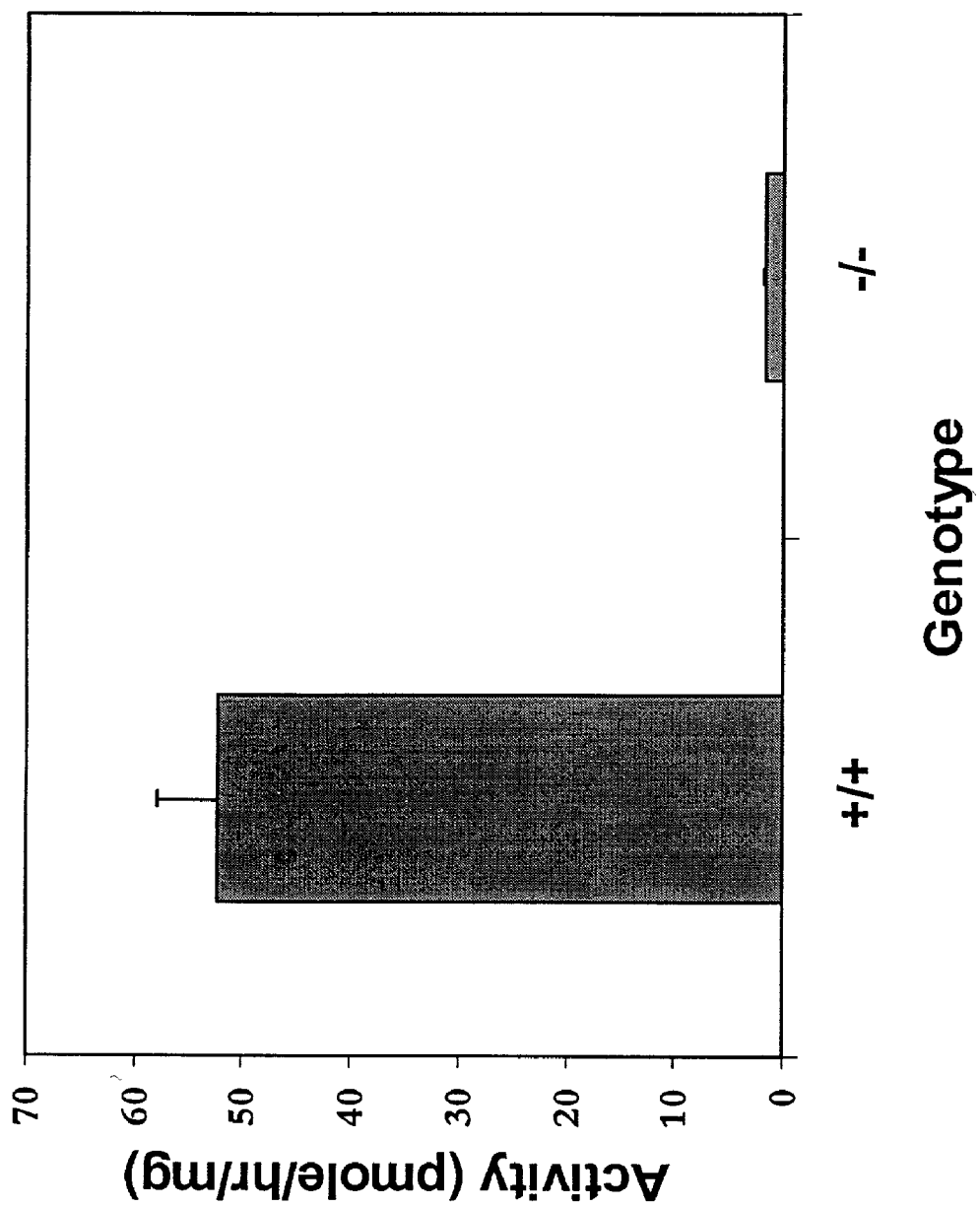

To confirm that BACE-1 is the major β-secretase enzyme in brain tissue, measurements of enzyme activity were made in P2 pellets from cortex of exon 1-disrupted BACE-1 knockout mice. See FIGS. 3A and 3B. Enzyme activity from P2 pellets of cortex from wild-type mice was linear relative to amount of protein added (data not shown) and fully inhabitable with a specific inhibitor of β-secretase activity (FIG. 3A, I1). The IC50 values for inhibition of enzymatic activity by two substrate analogue inhibitors (FIG. 3A), differing by one amino acid and 100,000-fold in affinity, corresponded in the P2 pellet to that in enzyme purified from human brain. Thus, the enzyme activity we are measuring in the P2 pellet behaves identically to purified BACE-1 activity. Although robust activity was observed in wild-type mice, no activity was detectable in cortical extracts from −/− knockout mice (FIG. 3B). This indicates BACE-1 is the major β-secretase in intact mouse brain tissue.

We demonstrate that BACE-1 knockout mice are generally healthy and that they lack the major β-secretase in brain. To do so, we generated two independent lines of BACE-1 knockout mice and studied these animals using biochemical, histological, clinical chemistry and behavioral techniques. Loss of BACE-1 ablated β-secretase activity and reduced Aβ production, yet these mice have no gross deficiencies in physiology or basic behaviors. Specifically, these mice develop normally in utero, as the knockout allele is inherited in a ratio expected by Mendelian genetics. No clearly genotypic abnormalities were noted upon assessment of fresh tissues nor upon histological examination of brain from young and adult animals. Taken together, these findings indicate that the BACE-1 gene is dispensable for development and function through early adulthood.

Because brain contains higher levels of β-secretase activity than other tissues, performance in behavioral paradigms was used as a sensitive measure of brain function. Preliminary behavioral evaluation of homozygous and heterozygous BACE-1 knockout mice revealed no obvious functional abnormalities when compared to wild-type littermates. Loss of BACE-1 activity does not induce strong hyperactivity, behavioral sedation, or other locomotor defects. In addition, gross behavioral observations and tests of neuromuscular activity showed no obvious deficits in basal neurological and physiological functions in these animals. These results are preliminary, and we are currently carrying out further detailed behavioral analyses on larger numbers of mice of both sexes and under different conditions to detect more subtle effects.

Importantly, β-secretase activity is undetectable in primary cortical cultures and in brains of homozygous BACE-1 knockout mice, indicating that BACE-1 is the major β-secretase enzyme in mouse brain. Moreover, BACE-1 is also likely the major β-secretase in human brain. Clearly, loss of BACE-1 results in a large decrease in Aβ production in primary cortical cultures. The small amount of detectable Aβ observed in the knockout cultures may represent forms initiating past the initial Asp of Aβ, since it was necessary to use an ELISA detecting all forms of Aβx-40 to detect Aβ production from endogenous murine APP. Alternatively, because the cortical cultures contained both neuronal and glial cells, the small amount of Aβ may result from low activity of another enzyme, e.g. BACE2, although β-secretase activity of BACE2 has not yet been demonstrated in vivo. Nevertheless, these data further demonstrate that BACE-1 is the major β-secretase required for production of Aβ.

Our data indicate that pharmacological inhibition of BACE-1 activity will greatly diminish production of Aβ. It follows, then, that small-molecule BACE-1 inhibitors should prevent the accumulation of amyloid plaque in the brain of individuals with Alzheimer's disease and may prevent growth of pre-existing plaques. Notably, loss of BACE-1 activity is well tolerated in mice, as no profound defects were found through four months of age. Although we have not yet evaluated aged mice, the overall healthy phenotype of BACE-1 knockout animals suggests that BACE-1 inhibition is unlikely to produce serious untoward effects.

Over the past 15 years, since the description of APP and elucidation of its relationship to Aβ, there has been an exhaustive search for the putative enzymes responsible for catabolism of APP to Aβ. Although the γ-secretase enzyme has not been conclusively identified, it appears to be associated with presenilins. Discovery of the BACE-1 enzyme has provided a characterized molecular target that can be studied as a possible avenue to interdict Aβ-mediated neurotoxicity in AD. Knockout of BACE-1 function does not lead to profound developmental abnormalities nor biochemical or behavioral dysfunction post-natally. This contrasts with perturbation of presenilin function, which leads to significant developmental abnormalities. At this point, the evidence suggests that BACE-1 is an excellent therapeutic target for development of AD pharmacotherapeutics and that small-molecule inhibitors of this enzyme may be useful in halting the initiation and progression of AD.

The BACE-1 knockout mouse could also be used to test and evaluate the toxicity, structure activity relationship and usefulness of compounds that may be potential BACE-1 inhibitors.

We also generated crosses between beta-secretase knockout mice and PDAPP mice as described by Games et al., supra. Mice that were heterozygous for nonfunctional BACE-1 were crossed with homozygous PDAPP to produce mice that were heterozygous for both nonfunctional BACE-1 and a FAD mutated APP transgene (heterozygous BACE-1, PDAPP mice). Mice with this genotype were then interbred to generate mice that are Ir homozygous for nonfunctional BACE-1 and for a FAD mutated APP transgene (homozygous BACE-1 PDAPP mice).

A significant decrease in beta-secretase levels was observed heterozygote mice (32% in seven-day old mice and 52% in one month old mice). Aβ levels were reduced by 15–18% and 12% respectively in the two sets of mice. The decrease in the one month old mice was significant by Mann Whitney and Student's t test. A slightly smaller decrease was observed in Aβ 42, which was significant by Mann Whitney but not Student's t test. A significant increase was observed in combined levels of full length APP and secreted APP.

The increase in APP in the heterozygous animal is larger and more significant that the decrease in Aβ. The increase in APP is consistent with the decrease in beta secretase activity, and suggests that beta secretase cleavage of endogenous APP in the PDAPP mouse brain more closely correlates with BACE-1 activity than does the final production of Aβ. The relatively weak correlation between level of beta-secretase and level of Aβ suggests that the level of Aβ is determined in part by other factors, such as turnover and or subsequent processing, such as by gamma secretase.

Levels of Aβ and beta secretase were both undetectable in homozygous mice (i.e., homozygous for a nonfunctional BACE-1 allele and mutant APP allele).

Materials and Methods

Generation of BACE-1 targeted ES cells (exons 4-8). The targeting vector was designed in a way that, upon homologous recombination, exons 4 to 8 of the BACE-1 gene are flanked with FLP recombinase target sites (frt sites). With respect to the genomic locus, the 5' region of homology covered 4.5 kb and the 3' region 4.3 kb until the third frt site, and an additional 1.5 kb further 3'. Selection for homologous recombination was achieved by inserting a frt-flanked neomycin resistance cassette between exons 3 and 4 of the BACE-1 gene. The parental embryonic stem (10) cell line E14 (129/Ola) was employed for successful targeting of the BACE-1 locus. Following electroporation, recombinant cells were positively selected with G418 (Geneticin, Gibco/BRL). Successful targeting of the BACE-1 gene and integration of the third frt site was detected in resistant ES clones by HpaI restriction enzyme digestion and Southern hybridization employing a 3' external probe B. Probe B was generated by PCR from mouse genomic DNA using primers 5'-GACAGATGAATTCCTATCTTG-3' (SEQ. ID. NO. 1) and 5'-GTCTCTTCCTCATCAACTGTC-3' (SEQ. ID. NO. 2). Single integration of one targeting vector was confirmed. ES cells with appropriate targeting were injected into blastocysts from C57BL/6 mice. Chimeric offspring were bred with C57BL/6 mice to produce animals heterozygous for the flp-targeted BACE-1 allele. These mice were bred with mice transgenic for flp recombinase expressed under control of a CMV enhancer/chicken actin promoter on a C57BL/6×CBA background for the in vivo deletion of the selection marker.

Figure 1C:
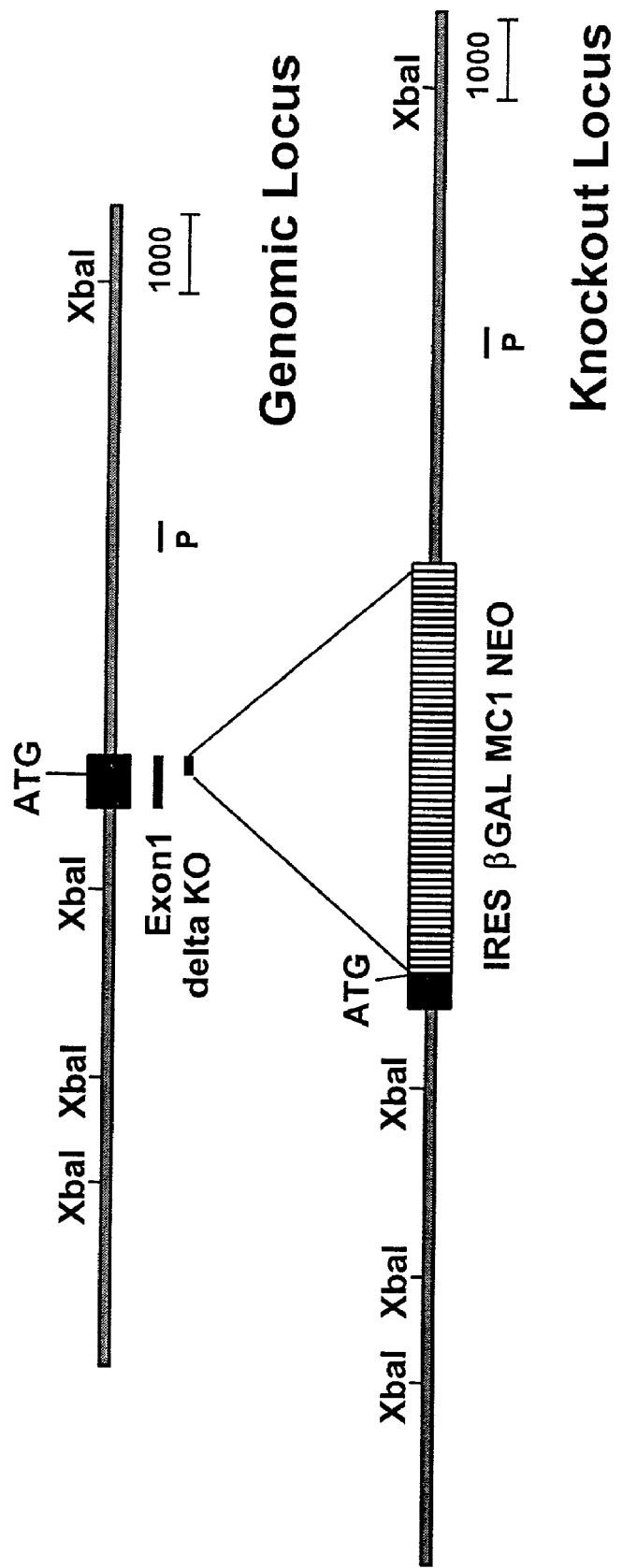

Generation of exon 1 BACE-1 knockout mice. A lambda KOS genomic clone encoding BACE-1 from murine strain 129/SvEvBrd covering 5.3 kb upstream and 2.5 kb downstream of exon 1 were used to generate the knock-out targeting vector. See, Wattler et al. *Biotechniques*, 26, 1150–1160 (1999). (FIG. 1C). A 165 base pair deletion of exon 1 starting from 2 base pairs past the initiating methionine and extending through the end of exon 1 was replaced with an expression cassette in the targeting vector. A neomycin resistance gene was included for positive selection of homologous recombinants and HSV-thymidine kinase gene for negative selection against random integrants. The targeting vector was electroporated into 129/SvEvBrd ES cells and clones were selected positively for neomycin resistance with G418 (Geneticin, Gibco/BRL) and negatively against thymidine kinase with gancyclovir (Roche). Clones were screened for homologous recombination by Southern analysis using XbaI digestion and hybridized with probe P shown in FIG. 1C. Probe P was generated by PCR from mouse genomic DNA using primers 5'-CGGAGCCCAACTGT-CAAAAAG-3' (SEQ. ID. NO. 3), and 5'-CCAACCGTGC-CCTCCTGC-3' (SEQ. ID. NO. 4). Recombination was confirmed by digestion of genomic DNA with Pvu II and hybridization with a probe generated by PCR from mouse genomic DNA using primers 5'-GTGTCATGTAACTCAG-GCTG-3' (SEQ. ID. NO. 5), and 5'-GGTAATCTATGCA-GAGCACTTG-3' (SEQ. ID. NO. 6). Single integration of one targeting vector was confirmed. ES cells with appropriate targeting were injected into blastocysts from C57B1/6 albino mice. Chimeric offspring were bred with C57B1/6 albino mice to produce animals heterozygous for the BACE-1 knockout allele. Heterozygous mice were bred together to generate mice homozygous for the knockout allele. Genotyping on experimental mice was reconfirmed on tissue taken at the time of sacrifice.

Aβ Elisa. The Aβ Elisa for Aβx-40 was performed as described in Johnson-Wood et al., *Proc. Natl. Acad. Sci. U.S.A.*, 94, 1550–1555 (1997), except that antibody 2G3 was used as capture and coated at 10 micrograms/ml and antibody 266 was used as reporter at 1 microgram/ml. Rodent Aβ was used for the standard and the same medium used for culturing of the primary cortical cells was added to the standard reaction in dilutions equivalent to that of the samples assayed.

Cortical brain cultures. Male and female heterozygous (+/−) BACE-1 exon 1-disrupted mice were bred together and E16 mouse fetuses obtained from timed pregnancies. Primary cortical cultures were generated from cortexes of individual fetuses, and the hindquarters of each fetus were used for genotyping as described above. The cerebral cortex of E16 mouse fetuses was dissected from each pup individually and triturated and trypsinized to make a single cell suspension. The cells were plated in polyethylenimine-coated 24 well plates at a density of 625,000 cells/well in neuronal medium (MEM, Gibco) containing 5% fetal bovine serum (Gibco) and 5% Chang's supplement (Irvine Scientific). After 4–5 days in vitro the medium was changed and the cells incubated for an additional 1–3 days before harvesting the conditioned medium for Aβ ELISA.

β-secretase activity assays on cultured cells. Primary cultured cortical cells were washed in PBS, lysed in extraction buffer (1 mM HEPES, pH7.5, 1 mM EDTA 0.2% Triton X-100, 1 mM PMSF, 10 micrograms/ml E-64 and 10 micrograms/ml Pepstatin A) and centrifuged in a microfuge at 14,000 rpm for 5 minutes. Aliquots of supernatant were assayed directly for β-secretase activity using as substrate a construct containing the bacterial maltose binding protein fused to the C-terminal 125 amino acids of APP. Enzymatic assays incubated for 2 hours at 37° C. Total cellular protein was less than 2.5 micrograms per reaction, and activity was linear with amount of protein added.

β-secretase activity assays in brain homogenates. Cortex was dissected, weighed and frozen from mice shortly after sacrifice. All subsequent operations were performed at 4° C. or on ice. Mouse cortex were homogenized in 4 ml of homogenization buffer (250 mM sucrose, 2 mM EDTA, 20 mM HEPES, pH 7.5) per gram of brain. The homogenates were centrifuged at 1,000×g for 20 minutes. The supernatants were saved, and the pellets were resuspended in homogenization buffer and centrifuged as before. The supernatants were pooled with the respective first supernatants, and centrifuged at 16,000×g for 20 minutes. The resulting pellets (P2) were extracted with 1.5 ml of P2 extraction buffer (150 mM sodium chloride, 2 mM EDTA, 0.5% Triton X-100, 20 mM MES, pH 6.0, 5 microgram/ml leupeptin, 2 microgram/ml E64, 1.0 µg/ml pepstatin, 0.2 mM PMSF) for 1 hour with agitation. The suspensions were centrifuged at 16,000×g for 20 minutes. The extracted supernatants were neutralized with Tris base and assayed for β-secretase activity using as substrate a construct containing the bacterial maltose binding protein fused to the C-terminal 125 amino acids of APP, except that enzyme assay reactions were incubated for 2 hours at 37° C. and were diluted ⅕ prior to ELISA assay. Enzyme activity was normalized to amount of protein from the P2 pellet assayed. Human BACE-1 control was purified from brain as previously described. See. Sinha Nature, 402, 537–540 (1999).

Gross behavioral observations and measurement of open field activity. Visual observation and scoring for physical and physiological function were done as per an amended version of the "SHIRPA" test. Measurement of horizontal activity was performed in Digiscan activity boxes equipped with photocells.

Animal handling. All animal work used protocols approved by the institutional animal care and use committee. Prior to behavioral observations and necropsy, exon 1-disrupted animals were acclimated for six days in metabolism cages to collect urine. Urine was collected over a 24-hour period on four consecutive days. Urinalysis parameters included volume, specific gravity, pH, protein, glucose, ketones, occult blood, urobilinogen, icto-test and urinary sediment. At necropsy, mice were anesthetized with isofluorane and exsanguinated through the posterior vena cava for complete blood counts and serum chemistries. Complete blood counts included standard quantitative cell count measures, differential, and morphological evaluation of the smear. Serum chemistry values included BUN, glucose, creatinine, cholesterol, alanine aminotransferase, aspartyl aminotransferase, alkaline phosphatase, total protein, albumin, phosphorus, calcium, creatine kinase, sodium, potassium, chloride, triglycerides, total bilirubin, and direct bilirubin. A CBC was performed on exon 4-8-deleted animals in Table 1.

A detailed gross necropsy examination was performed. Terminal body weights and weights of brain, kidney, adrenals, thymus, liver, testes or ovaries were collected. Mice were perfused through the left ventricle with heparinized 0.9% saline to facilitate biochemical assays on brain tissue. The brain was removed, laterally bisected, and the right half dissected into cortex, hippocampus, cerebellum, and midbrain and frozen for biochemical assays. The left half of the brain was immersion fixed in 4% paraformaldehyde. Multiple sections of brain (cerebellum, brain stem, cortex, hippocampus, thalamus, and olfactory lobe) were examined.

TABLE 1

BACE-1 knockout animals examined by necropsy and histology. Exon 1-disrupted animals were also used for behavioral observations.

| Genotype | Age (weeks) | Males | Females |
|---|---|---|---|
| Exon 1 | | | |
| −/− | 7–17 | 8 | 2 |
| +/− | 7–13 | 10 | 0 |
| +/+ | 8–17 | 3 | 7 |
| Exons 4–8 | | | |
| −/− | 6 | 1 | 0 |
| +/− | 6 | 1 | 1 |
| +/− | 2 | 1 | 5 |
| +/+ | 6 | 0 | 1 |
| +/+ | 2 | 1 | 0 |

While the foregoing invention has been described in some detail for purposes of clarity and understanding, it will be clear to one skilled in the art from a reading of this disclosure that various changes in form and detail can be made without departing from the true scope of the invention. The above examples are provided to illustrate the invention, but not to limit its scope; other variants of the invention will be readily apparent to those of ordinary skill in the and are encompassed by the claims of the invention. The scope of the invention should, therefore, be determined not with reference to the above description, but instead should be determined with reference to the appended claims along with their full scope of equivalents. All publications, references, and patent documents cited in this application are incorporated by reference in their entirety for all purposes to the same extent as if each individual publication or patent document were so individually denoted.

What is claimed is:

1. A transgenic mouse whose genome comprises homozygous non-functional beta-secretase-1 (BACE-1) genes, wherein the genes comprise a deletion in exons 4–8 of the BACE-1 gene and the mouse lacks functional BACE-1.

2. The transgenic mouse of claim 1, wherein the mouse or an ancestor thereof was produced by homologous recombination between an endogenous BACE-1 gene and a construct containing a positive selection marker flanked by segments showing sufficient sequence relatedness to the BACE-1 gene for the construct to recombine with the endogenous allele introducing the positive selection marker into the BACE-1 gene and rendering the gene nonfunctional.

3. The transgenic mouse of claim 1, wherein the mouse or an ancestor thereof was produced by homologous recombination between an endogenous BACE-1 gene and a construct containing a positive selection marker flanked by segments showing sufficient sequence relatedness to the BACE-1 gene to undergo homologous recombination with it, these segments being flanked by frt recombination sites, whereby the construct recombines with the endogenous gene introducing the positive selection marker and frt recombination sites into the endogenous gene, and the frt recombination sites undergo recombination with each other thereby excising DNA between the flp recombination sites resulting in a deleted nonfunctional BACE-1 gene.

4. The transgenic mouse of claim 1, wherein the gene is rendered nonfunctional by homologous recombination with a targeting vector comprising a lambda KOS genomic clone of BACE-1.

5. The transgenic mouse of claim 1, whose genome further comprises a transgene comprising a DNA sequence encoding an APP having a familial Alzheimer's disease mutation.

6. The transgenic mouse of claim 5, wherein the transgene comprises a mutation at codons 595 and 596 of human APP695, or an isoform or fragment thereof, wherein the amino acid residues at positions corresponding to positions 595 and 596 are asparagine and leucine, respectively.

7. The transgenic mouse of claim 5, wherein the transgene comprises a mutation at codon 717 of APP770 or an isoform or fragment of APP770 having a mutant amino acid residue at position 717.

8. The transgenic mouse of claim 5, wherein the mutant amino acid residue is isoleucine, phenylalanine or glycine.

9. The transgenic mouse of claim 5, wherein the mouse is homozygous for the non-functional BACE-1 gene.

10. The transgenic mouse of claim 5, wherein the mouse is heterozygous for the transgene.

11. A cortical cell culture derived from the transgenic mouse of claim 1, wherein the cells lack functional BACE-1.

12. The cortical cell culture of claim 11, wherein the cell culture is a primary cell culture.

13. The cortical cell culture of claim 11, wherein the cell culture comprises a detectable amount of a peptide recognized by an antibody that recognizes residues 13–28 of Aβ.

14. The cortical cell culture of claim 13, wherein the peptide recognized by an antibody that recognizes residues 13–28 of Aβ is β-amyloid.

15. A method for screening for an inhibitor of the production of an Aβ peptide by a protease other than BACE-1, wherein the peptide is recognized by an antibody that recognizes residues 13–28 of Aβ comprising:

exposing a transgenic whose genome comprises homozygous non-functional BACE-1 genes, wherein the mouse lacks functional BACE-1, or a cortical cell culture derived from the mouse, wherein the cells lack functional BACE-1 to an agent, and detecting the production of an Aβ with an antibody that recognizes residues 12–28 of Aβ, wherein a reduced amount of Aβ peptide produced in the exposed transgenic mouse or cortical cell culture relative to the transgenic mouse or the cortical cell culture not exposed to the agent is indicative of inhibitory activity.

16. The method of claim 15, wherein a cortical cell culture is exposed to the agent.

17. The method of claim 15, wherein the cortical cell culture is a primary cell culture.

18. The method of claim 15, wherein the peptide recognized by an antibody that recognizes residues 13–28 of Aβ is β-amyloid.

19. A method of analyzing potential side effects for an inhibitor of β-secretase comprising:

exposing a transgenic mouse whose genome comprises homozygous non-functional allele BACE-1 genes, wherein the mouse lacks functional BACE-1, or a cortical cell culture derived from the mouse where the cells lack functional BACE-1 to an inhibitor of BACE-1; and measuring whether there is a change in the level of at least one component of the transgenic mouse or cortical cell in response to the administration of the inhibitor relative to the transgenic mouse or the cell culture not exposed to the agent; wherein a change in level of at least one component indicates a potential side effect of the inhibitor.

20. The method of claim 19, wherein the measuring step measures changes in the levels of a plurality of mRNA species.

21. A mouse embryonic stem cell whose genome comprises a non-functional gene for BACE-1 genes, wherein the gene comprises a deletion in exons 4–8 of the BACE-1 gene.

22. The mouse embryonic stem cell of claim 21, wherein the cell is homozygous for the deletion of the BACE-1 gene.

23. The mouse embryonic stem cell of claim 21 produced by homologous recombination with a targeting vector designed in a way that, upon homologous recombination, exons 4 to 8 of the BACE-1 gene are flanked with FLP recombinase target sites (frt sites).

24. The mouse embryonic stem cell of claim 23, produced by homologous recombination with a targeting vector designed in a way that, with respect to the genomic locus, the 5' region of homology covered 4.5 kb and the 3' region 4.3 kb until the third frt site, and an additional 1.5 kb further 3'.

25. The mouse embryonic stem cell of claim 21 that is homozygous for a nonfunctional BACE-1 gene lacking exons 4–8 of BACE-1.

26. The mouse embryonic stem cell of claim 21, produced by homologous recombination with a first targeting vector that introduces a neomycin resistance gene in the BACE-1 gene and with a second targeting vector that replaces the neomycin resistance gene with a hygromycin resistance gene cassette.

27. A blastocyst produced by insertion of the mouse embryonic stem cell of claim 21.

28. A method for generating a transgenic mouse comprising at least one nonfunctional BACE-1 gene, the method comprising:

introducing at least one genetic construct into a mouse embryonic stem cell, the genetic construct comprising a positive selection marker flanked by segments showing sufficient sequence relatedness to the BACE-1 gene to undergo homologous recombination with it, these segments being flanked by frt recombination sites;

screening for cells in which recombination has occurred between the genetic construct and the endogenous gene;

injecting the mouse embryonic stem cells, which have undergone recombination, into blastocysts to generate chimeric mice; developing the chimeric blastocysts into chimeric mice;

breeding the chimeric mice with mice of the type which provided the blastocysts to generate mice heterozygous for the nonfunctional gene of BACE-1; and breeding the mice heterozygous for the nonfunctional BACE-1 gene with mice transgenic for flp recombinase resulting in transgenic mice whose genome comprises a nonfunctional BACE-1 gene.

29. The method of claim 28, wherein the gene is rendered nonfunctional by deletion of at least a segment of exon 1.

30. The method of claim 28, wherein the gene is rendered nonfunctional by deletion of exons 4–8.

31. A transgenic mouse comprising at least one nonfunctional BACE-1 gene, wherein the mouse or an ancestor thereof was produced by homologous recombination between an endogenous BACE-1 gene and a construct containing a positive selection marker flanked by segments showing sufficient sequence relatedness to the gene to undergo homologous recombination with it, these segments being flanked by frt recombination sites, whereby the construct recombines with the endogenous gene introducing the positive selection marker and frt recombination sites into the endogenous gene, and the frt recombination sites undergo recombination with each other thereby excising DNA between the flp recombination sites resulting in a nonfunctional endogenous BACE-1 gene.

32. The transgenic mouse of claim 31, wherein the mouse is homozygous for the nonfunctional endogenous BACE-1 gene.

33. The transgenic mouse of claim 31, wherein the gene is rendered nonfunctional by deletion of at least a segment from an exon 1.

34. The transgenic mouse of claim 31, wherein the gene is rendered nonfunctional by deletion of at least a segment from exon 1.

35. The transgenic mouse of claim 31, wherein the gene is rendered nonfunctional by a 165 base pair deletion of exon 1 starting from 2 base pairs past the initiating methionine and extending through the end of exon 1 replaced with an expression cassette in the targeting vector electroporated into 129 ES cells to generate the transgenic mouse.

36. The transgenic mouse of claim 31, wherein the gene is rendered nonfunctional by deletion of exons 4–8.

37. The transgenic mouse of claim 31, whose genome further comprises a transgene comprising a DNA sequence encoding an APP having a familial Alzheimer's disease mutation.

38. The transgenic mouse of claim 37, wherein the transgene comprises a mutation at codons 595 and 596 of human APP695, or an isoform or fragment thereof, wherein the amino acid residues at positions corresponding to positions 595 and 596 are asparagine and leucine, respectively.

39. The transgenic mouse of claim 37, wherein the transgene comprises a mutation at codon 717 of APP770 or an isoform or fragment of APP770 having a mutant amino acid residue at position 717.

40. The transgenic mouse of claim 37, wherein the mutant amino acid residue is isoleucine, phenylalanine or glycine.

41. A cortical cell culture derived from the transgenic mouse of claim 31, wherein the cells lack functional BACE-1.

42. The cortical cell culture of claim 31, wherein the cell culture is a primary cell culture.

43. The cortical cell culture of claim 41, wherein the cell culture comprises a detectable amount of a peptide recognized by an antibody that recognizes residues 13–28 of Aβ.

44. The cortical cell culture of claim 43, wherein the peptide recognized by an antibody that recognizes residues 13–28 of Aβ is β-amyloid.

* * * * *